US011531018B2

(12) United States Patent
Basheer et al.

(10) Patent No.: US 11,531,018 B2
(45) Date of Patent: *Dec. 20, 2022

(54) MODULAR SENSOR ARCHITECTURE FOR SOIL AND WATER ANALYSIS AT VARIOUS DEPTHS FROM THE SURFACE

(71) Applicant: urban-gro, Inc., Lafayette, CO (US)

(72) Inventors: Mohammed Rana Basheer, Costa Mesa, CA (US); Atul A. Patel, Irvine, CA (US)

(73) Assignee: URBAN-GRO, INC., Lafayette, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/164,098

(22) Filed: Feb. 1, 2021

(65) Prior Publication Data

US 2021/0156838 A1   May 27, 2021

Related U.S. Application Data

(63) Continuation of application No. 16/519,800, filed on Jul. 23, 2019, now Pat. No. 10,955,402, which is a continuation-in-part of application No. 15/626,079, filed on Jun. 17, 2017, now Pat. No. 10,405,069, and a continuation-in-part of application No. 15/626,085, filed on Jun. 17, 2017, now Pat. No. 10,499,123.

(60) Provisional application No. 62/351,989, filed on Jun. 19, 2016.

(51) Int. Cl.
*G01N 33/24*   (2006.01)

(52) U.S. Cl.
CPC ................... *G01N 33/246* (2013.01)

(58) Field of Classification Search
None
See application file for complete search history.

(56) References Cited

U.S. PATENT DOCUMENTS

| 4,492,111 A * | 1/1985 | Kirkland | ................ G01N 33/24 73/9 |
| 4,567,563 A * | 1/1986 | Hirsch | .................... A01G 25/16 40/608 |
| 4,845,978 A * | 7/1989 | Whitford | ................ G01N 25/18 73/75 |

(Continued)

FOREIGN PATENT DOCUMENTS

| WO | WO-2015038991 A1 * | 3/2015 | ............. G01N 21/01 |
| WO | WO-2017051393 A1 * | 3/2017 | ......... G01N 33/0098 |

*Primary Examiner* — Muhammad Adnan
(74) *Attorney, Agent, or Firm* — Polsinelli PC (57) ABSTRACT

A method of analyzing soil using a modular sensor device. The modular sensor device including a sensor bus head, a sensor bus terminus, and a sensor rod in a stacked arrangement. The sensor rod disposed between the sensor bus head and the sensor bus terminus. The method including setting on an output pin of the sensor bus. The method further including, subsequent to setting the output pin of the sensor bus, detecting a transition on an input pin of the sensor rod, the output pin of the sensor bus and the input pin of the sensor rod being part of a daisy chain. The method further including, in response to detecting the transition at the input pin of the sensor rod, enabling bidirectional communication between the sensor rod and the sensor bus head over a communication bus electrically coupling the sensor bus head to the sensor rod.

9 Claims, 7 Drawing Sheets

(56) References Cited

U.S. PATENT DOCUMENTS

| | | | | |
|---|---|---|---|---|
| 4,852,054 A * | 7/1989 | Mastandrea | G01F 23/804 | 73/40 |
| 4,922,945 A * | 5/1990 | Browne | A01G 25/167 | 239/63 |
| 5,000,051 A * | 3/1991 | Bredemeier | G01N 1/14 | 73/864.74 |
| 5,121,993 A * | 6/1992 | Carrigan | G01V 9/005 | 374/43 |
| 5,156,179 A * | 10/1992 | Peterson | A01G 25/167 | 251/63.5 |
| 5,179,347 A * | 1/1993 | Hawkins | G01N 27/121 | 324/696 |
| 5,644,947 A * | 7/1997 | Hubbell | G01N 33/246 | 73/73 |
| 5,758,538 A * | 6/1998 | Hubbell | G01N 7/10 | 73/73 |
| 5,819,850 A * | 10/1998 | Lee, Jr. | E21B 33/13 | 175/21 |
| 5,915,476 A * | 6/1999 | Hubbell | E21B 49/08 | 166/205 |
| 5,941,121 A * | 8/1999 | Faybishenko | E21B 47/06 | 73/73 |
| 6,119,535 A * | 9/2000 | Tambo | G01F 23/243 | 73/865.8 |
| 6,164,179 A * | 12/2000 | Buffman | F41F 3/07 | 114/316 |
| 6,308,563 B1 * | 10/2001 | Hubbell | E21B 47/06 | 73/152.51 |
| 6,317,694 B1 * | 11/2001 | Kram | E21B 49/00 | 702/11 |
| 6,405,588 B1 * | 6/2002 | Hubbell | E21B 49/00 | 166/113 |
| 6,531,965 B1 * | 3/2003 | Kaiser | F42B 12/365 | 102/513 |
| 6,532,803 B2 * | 3/2003 | Hutchinson | G01N 33/246 | 73/73 |
| 6,539,780 B2 * | 4/2003 | Hubbell | E02D 1/06 | 73/152.55 |
| 6,647,799 B1 * | 11/2003 | Raper | E02D 1/022 | 73/73 |
| 6,752,007 B1 * | 6/2004 | Hubbell | G01N 7/10 | 73/826 |
| 6,942,043 B2 * | 9/2005 | Kurkoski | E21B 47/01 | 175/45 |
| 6,975,236 B2 * | 12/2005 | Staples | G08B 21/20 | 73/1.73 |
| 6,975,245 B1 * | 12/2005 | Slater | A01G 25/167 | 239/63 |
| 6,976,386 B1 * | 12/2005 | Grover | E21B 49/08 | 73/29.02 |
| 7,042,234 B2 * | 5/2006 | Buss | G01N 27/223 | 324/658 |
| 7,183,779 B2 * | 2/2007 | Hughes | G01N 33/246 | 324/696 |
| 7,201,060 B2 * | 4/2007 | Frost | G01N 3/48 | 73/9 |
| 7,311,011 B2 * | 12/2007 | Clark | G01N 1/14 | 73/864.74 |
| 7,705,616 B2 * | 4/2010 | Hawkins | G01N 33/246 | 324/696 |
| 7,788,970 B2 * | 9/2010 | Hitt | A01G 25/167 | 73/73 |
| 8,058,885 B2 * | 11/2011 | Caron | G01N 27/048 | 324/453 |
| 8,444,937 B2 * | 5/2013 | Tuli | G01V 9/00 | 422/534 |
| 8,461,851 B2 * | 6/2013 | Iskander | G01N 33/24 | 324/637 |
| 8,793,024 B1 * | 7/2014 | Woytowitz | A01G 25/167 | 239/723 |
| 8,977,400 B1 * | 3/2015 | Porter | A01G 25/165 | 239/69 |
| 8,978,447 B2 * | 3/2015 | Caron | G01N 33/24 | 73/73 |
| 8,981,946 B2 * | 3/2015 | Runge | A01G 25/167 | 700/282 |
| D747,939 S * | 1/2016 | Behar | D8/1 | |
| 9,234,973 B2 * | 1/2016 | Scarlatti | B64C 27/51 | |
| 9,411,070 B2 * | 8/2016 | Chang | G01V 9/00 | |
| 9,465,020 B2 * | 10/2016 | Christian | G01N 9/00 | |
| 9,605,404 B2 * | 3/2017 | Hale | E02D 5/38 | |
| 9,606,087 B1 * | 3/2017 | Taylor | G01N 33/24 | |
| 9,784,887 B1 * | 10/2017 | Ulmer | B64D 1/08 | |
| 9,933,534 B2 * | 4/2018 | Talaalout | G01V 1/168 | |
| 10,405,069 B2 * | 9/2019 | Basheer | G01N 33/24 | |
| 10,681,862 B2 * | 6/2020 | Stoller | A01C 5/068 | |
| 11,116,154 B2 * | 9/2021 | Shakoor | A01G 25/167 | |
| 2003/0066357 A1 * | 4/2003 | Upadhyaya | G01N 3/58 | 73/818 |
| 2003/0074505 A1 * | 4/2003 | Andreas | G06F 13/4256 | 710/110 |
| 2003/0219062 A1 * | 11/2003 | Egidio | G01K 1/026 | 374/170 |
| 2003/0233885 A1 * | 12/2003 | Bird | G01F 15/003 | 73/861 |
| 2004/0200900 A1 * | 10/2004 | Hall | G06F 1/1656 | 235/400 |
| 2005/0120813 A1 * | 6/2005 | Clark | E21B 47/002 | 73/866.5 |
| 2005/0157843 A1 * | 7/2005 | Chen | G01N 33/1813 | 378/66 |
| 2005/0196111 A1 * | 9/2005 | Burdick | H04B 10/07 | 385/92 |
| 2006/0030971 A1 * | 2/2006 | Nelson | A01G 25/165 | 700/284 |
| 2007/0069115 A1 * | 3/2007 | Huang | G01B 11/18 | 250/227.14 |
| 2008/0129495 A1 * | 6/2008 | Hitt | A01G 25/167 | 340/539.26 |
| 2008/0184827 A1 * | 8/2008 | Susfalk | G01D 9/005 | 73/866.5 |
| 2008/0257636 A1 * | 10/2008 | Payor | G01V 1/38 | 73/866.5 |
| 2009/0272205 A1 * | 11/2009 | Brown | G01L 19/0015 | 73/866.5 |
| 2009/0322357 A1 * | 12/2009 | Beaulieu | G01V 3/088 | 324/692 |
| 2015/0168594 A1 * | 6/2015 | Chang | G01V 9/00 | 73/866 |
| 2015/0335288 A1 * | 11/2015 | Toth | A61B 5/6833 | 600/391 |
| 2015/0355152 A1 * | 12/2015 | Christian | G01N 17/00 | 702/2 |
| 2015/0379854 A1 * | 12/2015 | Kors | H04Q 9/00 | 340/618 |
| 2017/0241973 A1 * | 8/2017 | Chan | H04Q 9/00 | |
| 2017/0254766 A1 * | 9/2017 | Bermudez Rodriguez | G01N 27/301 | |
| 2018/0035606 A1 * | 2/2018 | Burdoucci | H04N 5/232935 | |
| 2018/0080861 A1 * | 3/2018 | Lafian | G01N 33/246 | |
| 2018/0156770 A1 * | 6/2018 | Saez | G01N 33/24 | |
| 2020/0132658 A1 * | 4/2020 | Koch | G01N 33/246 | |
| 2020/0149869 A1 * | 5/2020 | Egwu | G01B 11/02 | |
| 2020/0183104 A1 * | 6/2020 | Truong | G02B 6/4246 | |
| 2021/0109253 A1 * | 4/2021 | Ulmer | G01W 1/11 | |
| 2021/0195857 A1 * | 7/2021 | Haran | G01N 33/246 | |
| 2021/0223226 A1 * | 7/2021 | Grabbert | G01N 27/223 | |
| 2021/0263007 A1 * | 8/2021 | Chow | G01N 1/08 | |

* cited by examiner

MODULAR SENSOR ARCHITECTURE FOR SOIL AND WATER ANALYSIS AT VARIOUS DEPTHS FROM THE SURFACE

CROSS-REFERENCE TO RELATED APPLICATIONS

This application is a continuation of U.S. patent application Ser. No. 16/519,800 filed Jul. 23, 2019, which application is a continuation-in-part application of U.S. patent application Ser. No. 15/626,079, filed Jun. 17, 2017, now U.S. Pat. No. 10,405,069, which claims the benefit of U.S. Provisional Patent Application No. 62/351,989, filed Jun. 19, 2016. The subject matter of the aforementioned applications is hereby incorporated by reference in its entirety.

Application Ser. No. 16/519,800 is also a continuation-in-part application of U.S. patent application Ser. No. 15/626,085, filed Jun. 17, 2017, now U.S. Pat. No. 10,499,123, which claims the benefit of U.S. Provisional Patent Application No. 62/351,989, filed Jun. 19, 2016. The subject matter of the aforementioned applications is hereby incorporated by reference in its entirety.

TECHNICAL FIELD

The present invention generally pertains to soil and water analysis, and more specifically, to a modular sensor architecture for soil and water analysis at various depths from the surface.

BACKGROUND

Soil and water analysis for research, advisory services, formulation of recommendations, and designing appropriate soil management and water management practices is employed for various applications. Soil and water analysis may be conducted for estimating the availability of plant nutrients, geotechnical and ecological investigations, analyzing chemical composition of soil, determining soil moisture content, and measurement of various parameters in water bodies (e.g., pH, dissolved oxygen, oxidation-reduction potential, conductivity or salinity, temperature, turbidity, and dissolved ions such as fluoride, carbide, nitrates, lead, iodine, etc.).

Soil study is often conducted for analyzing soil composition for agronomic purposes. For many years, soil analysis has been used as an aid in assessing soil fertility and plant nutrient management. The soil analysis reports may provide information to set nutrient application targets, which are used to calculate manure and fertilizer application rates. Regular analysis from field sampling allows monitoring and detection of changes in the soil parameters over time, such as nutrients, pH, and salinity. Soil testing, in particular, is also important in monitoring the various types of land degradation and the choice of measures for land improvement. Development of effective and efficient analytical services of soil, water, plant, and fertilizers is thus important for increasing and sustaining land productivity, as well as crop and food production.

A variety of sensors, such as electromagnetic, optical, mechanical, electrochemical, airflow, and acoustic sensors, are conventionally available that can measure various parameters in soil and water. For instance, soil moisture sensors measure the volumetric water content in soil. Certain sensor probes measure temperature, pH, and electrical conductivity. Metal probes may measure the concentration of various elements, such as nitrogen, phosphorous, potassium, etc., in the soil and water.

Since one sensor can typically measure only one parameter, it is difficult to measure more than a single parameter at a time. Moreover, if two or more sensors are used to measure two different parameters, the quantity of the parameters at different levels cannot be ascertained. Accordingly, an improved sensor architecture and device that can analyze different parameters at varying depth may be beneficial.

Additionally, conventional sensors are designed as part of a single, non-stackable unit. Adding/removing sensors typically involves adding/removing chips from a socketed interface. Accordingly, an improved sensor architecture and bus system to accommodate the sensor architecture may be beneficial.

SUMMARY

Certain embodiments of the present invention may provide solutions to the problems and needs in the art that have not yet been fully identified, appreciated, or solved by conventional soil and water sensor technologies. For example, some embodiments of the present invention pertain to a sensor architecture for soil and water analysis at various depths.

In an embodiment, a modular sensor system includes a sensor bus head located at a top of the modular sensor system and a sensor bus terminus located at the bottom of the modular sensor system. The modular sensor system also includes at least one sensor rod connected between the sensor bus head and the sensor bus terminus. The at least one sensor rod is configured to determine environmental parameters of soil, water, or both, at its respective depth.

In another embodiment, a modular sensor system includes a sensor bus head configured to be located at a top of the modular sensor system. The sensor bus head includes a power and control interface configured to enable a user to select a function of the modular sensor system. The modular sensor system also includes a sensor bus terminus configured to be located at the bottom of the modular sensor system. The modular sensor system further includes at least one sensor rod configured to be connected between the sensor bus head and the sensor bus terminus. The at least one sensor rod is configured to determine environmental parameters of soil, water, or both, at its respective depth.

In yet another embodiment, a system includes a sensor bus head configured to be located at a top of the modular sensor system and a sensor rod configured to be connected with the sensor bus head and another sensor rod. The sensor rod is configured to determine environmental parameters of soil, water, or both, at its respective depth.

Certain embodiments of the present invention may provide solutions to the problems and needs in the art that have not yet been fully identified, appreciated, or solved by conventional bus technologies. For example, some embodiments of the present invention pertain to a sensor bus architecture for modular sensor systems.

In an embodiment, a modular sensor system includes a sensor bus that forms a top of the modular sensor system. The sensor bus head includes processing and control circuitry and a sensor select (SS) Out pin. The modular sensor system also includes a sensor bus terminus that forms a bottom of the modular sensor system. The sensor bus terminus includes an SS In pin. The modular sensor system further includes a first sensor module interconnectible between the sensor bus head and the sensor bus terminus. The first sensor module includes an SS Out pin and an SS In pin. The sensor bus head, the sensor bus terminus, and the first sensor module are interconnectable by a sensor bus, the sensor bus comprising sensor select (SS) lines. The SS Out pin of the sensor bus head is configured to be connected to the SS In pin of the first sensor module, and the SS Out pin of the first sensor module is configured to be connected to the SS In pin of the sensor bus terminus.

In another embodiment, a sensor bus head includes processing and control circuitry and an SS Out pin. The SS Out pin of the sensor bus head is connected to an SS Out line. The SS Out pin is configured to be connected to an SS In pin of a first sensor module. The processing and control circuitry is configured to set the SS Out pin of the sensor bus head to high to wake up the first sensor module, query the first sensor module to get sensor data, pass calibration information to the first sensor module, and when the sensor bus head is done with the first sensor module, instruct the first sensor module to wake up a next sensor module in a modular stack.

In yet another embodiment, a sensor module includes an SS Out pin and an SS In pin. The sensor module is interconnectable with a sensor bus head and other sensor modules via a sensor bus. The sensor bus includes SS lines. The SS Out pin of the sensor module is configured to be connected to an SS In pin of a next sensor module in a modular stack.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Some embodiments of the present invention pertain to a sensor architecture for soil and water analysis at various depths. The system of some embodiments determines chemical composition and measures concentration and/or environmental parameters, such as pressure, temperature, and/or moisture, at different depths. The system of some embodiments has a vertically stacked arrangement of a plurality of sensors interconnected through a bus network. Each of the sensors may be embedded in a rod with input and output connectivity. The sensor rod may be connected to other sensor rods, forming the vertically stacked arrangement. The uppermost sensor rod in the vertically stacked system may be connected to a sensor bus head, and the lowermost sensor rod may be connected to a sensor bus terminus. Between the sensor bus head and the sensor bus terminus, various sensor rods can be connected. Each senor rod may measure one or more specific parameters. The sensor(s) present in the sensor rod may be chemical composition analyzers, such as sensors for determining concentration of various elements, such as sodium, potassium, phosphorous, calcium, magnesium, sulfur, carbon, and/or other micro-nutrients or macro-nutrients. Additionally or alternatively, the sensors in the sensor rod may measure various environmental and/or chemical parameters, such as temperature, moisture, humidity, pH, pressure, electrical conductivity, salinity, turbidity, acidity, etc.

The system of some embodiments may be used to monitor and analyze soil and/or water. For measuring different parameters, different sensors embedded in different sensor rods may be interconnected between the sensor bus head at the top and the sensor bus terminus at the bottom. The system may then be inserted into the ground or placed in a body of water. In some embodiments that may operate in water, the sensor bus head may be buoyant enough such that the sensor bus head, sensor rod(s), and sensor bus terminus do not sink, and the sensor bus head floats at the surface (e.g., due to air-filled cavities, foam pockets, aerogel pockets, etc.). However, in certain embodiments, the sensor bus head, sensor rod(s) and sensor bus terminus may not be buoyant, and may be deployed in sediment at the bottom of a lake, river, or ocean, for instance. The sensors present at different depths in some embodiments sense the respective parameters for which they are designed and communicate the test results and the specific depth of the sensor to the sensor bus head. The results can then be used for further research and analysis of the soil and/or water.

The modular vertically stacked arrangement of the sensors in the system of some embodiments is provided such that the sensors are interconnected through a sensor bus network. The system may automatically detect the depth at which a particular sensor is positioned in the vertically stacked arrangement. Alternatively, the system may know the size of the rod, and the location of the sensor(s) thereon, and determine the location of the sensor(s) in that manner. The sensor bus communication scheme may allow hot-swapping of sensors and relatively low power operation for energy-constrained sensor data collection applications.

Figure 1A:
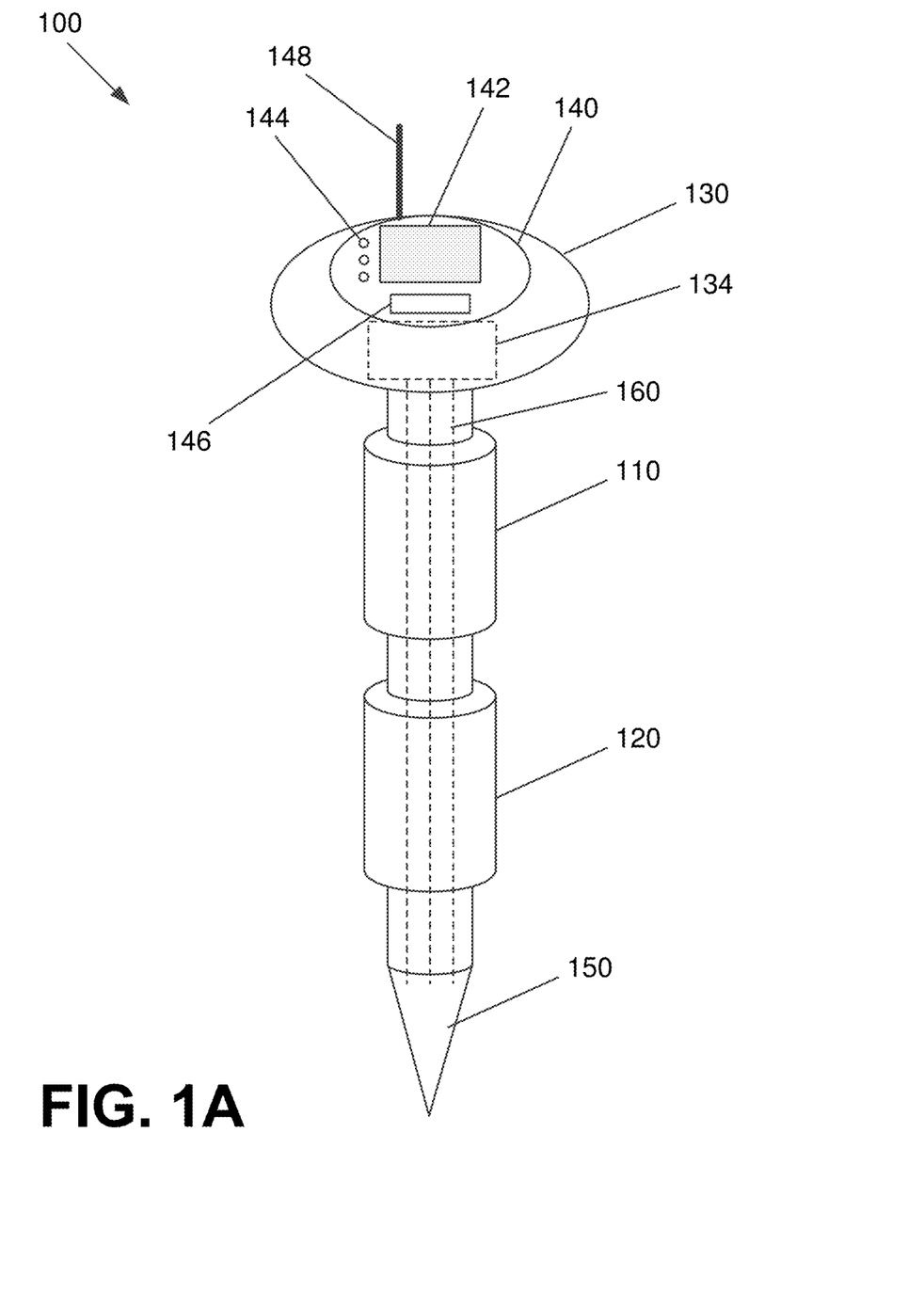
FIG. 1A is a perspective view illustrating a modular soil and water analysis device configured to perform soil and water analysis at different depths, according to an embodiment of the present invention.

FIG. 1A is a perspective view illustrating a modular soil and water analysis device 100 configured to perform soil and water analysis at different depths, according to an embodiment of the present invention. In this embodiment, device 100 includes two sensor rods 110, 120 that are vertically connected to one another. Sensor rod 110 is connected to sensor bus head 130 at an upper end thereof. Sensor rod 120 is connected to a sensor bus terminus 150 at the lower end thereof. Sensor bus terminus 150 helps to provide water resistance to the terminal of the bus, and in addition, provides the loading to identify the end of the sensor stack.

Sensor bus head 130 includes processing and control circuitry 134 (e.g., a microcontroller, transceiver, etc.) that facilitates operations of sensor bus head 130. Sensor bus head 130 also includes a power and control interface 140 in this embodiment. Power and control interface 140 includes a solar panel 142 to provide power to device 100, controls 144, and a display 146 for displaying various information to the user. For instance, controls 144 and display 146 may enable a user to select a function associated with device 100. Device 100 may be designed to enable analysis of soil and/or water at different depths. Results of the analysis may be provided on display 146. In certain embodiments, sensor bus head 130 may communicate analysis results to a central server using an antenna 148 that allows communication with other modular soil and water analysis devices, a cellular network, local area network (LAN), wide area network (WAN), satellite communications network, or any combination thereof, for instance. In certain embodiments, sensors of sensor rods 110, 120 may communicate their depth to sensor bus head 130. An interconnected bus network 160 runs between, and interconnects, the components of device 100.

Figure 1B:
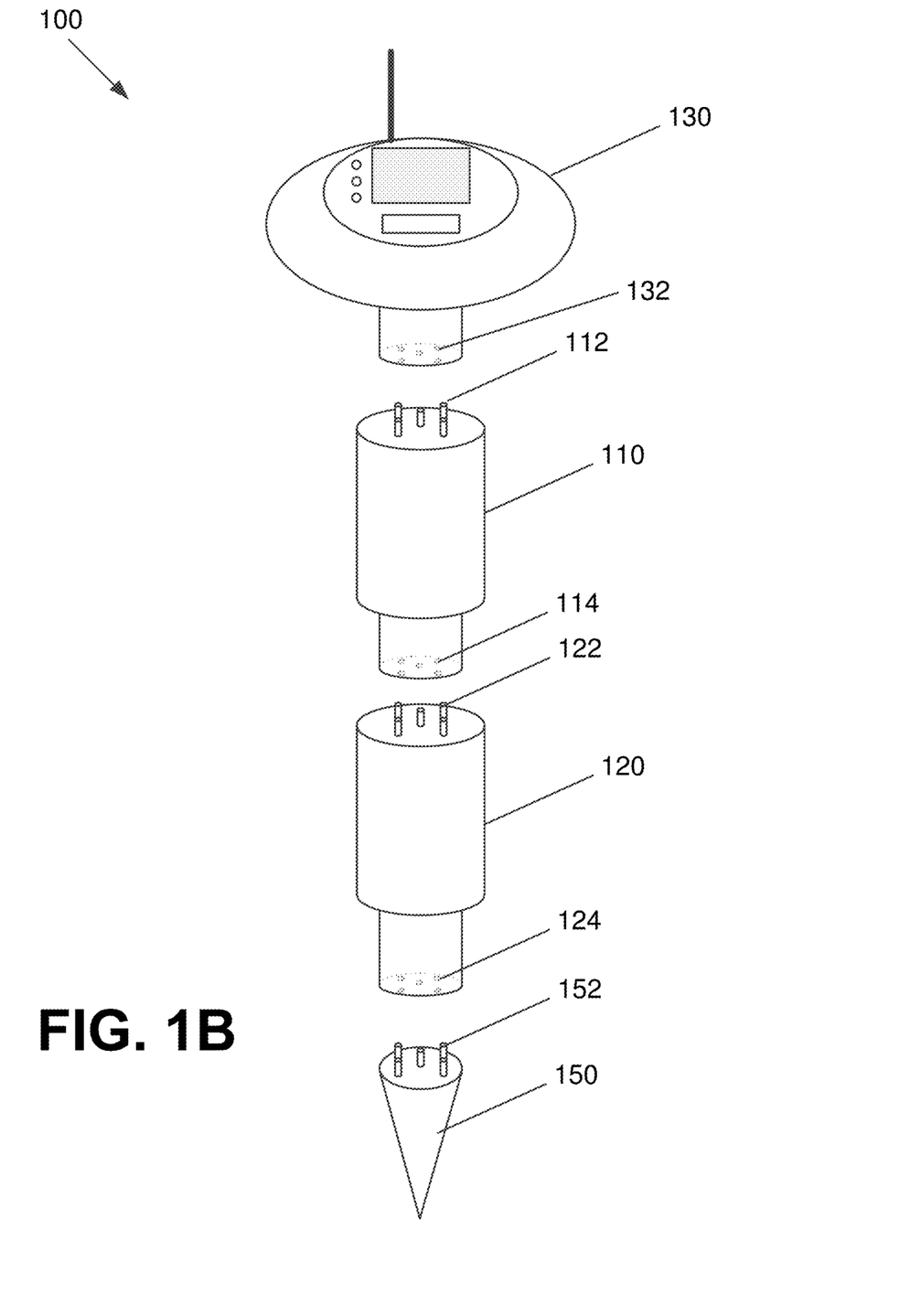
FIG. 1B is a perspective view illustrating disconnected components of the modular soil and water analysis device of FIG. 1A, according to an embodiment of the present invention.

FIG. 1B shows components of device 100 in a disconnected state. In this embodiment, sensor 110 connects to sensor bus head 130, sensor 120 connects to sensor 110, and sensor bus terminus connects to sensor 120 via male connectors 112, 122, 152, respectively (e.g., 5-pin waterproof male connectors), and female connectors 132, 114, 124, respectively (e.g., 5-pin female connectors). Alternatively, the male/female connectors may be reversed among the components (i.e., the female connectors may be on the top and the male connectors may be on the bottom), or some male connectors and some female connectors may be included on both the top and the bottom. Indeed, any suitable connectors and/or connection mechanism may be used to facilitate communication between the various components in other embodiments without deviating from the scope of the invention. As used herein, "pin" may be a port, a pin, or any other suitable connector without deviating from the scope of the invention.

Figure 2:
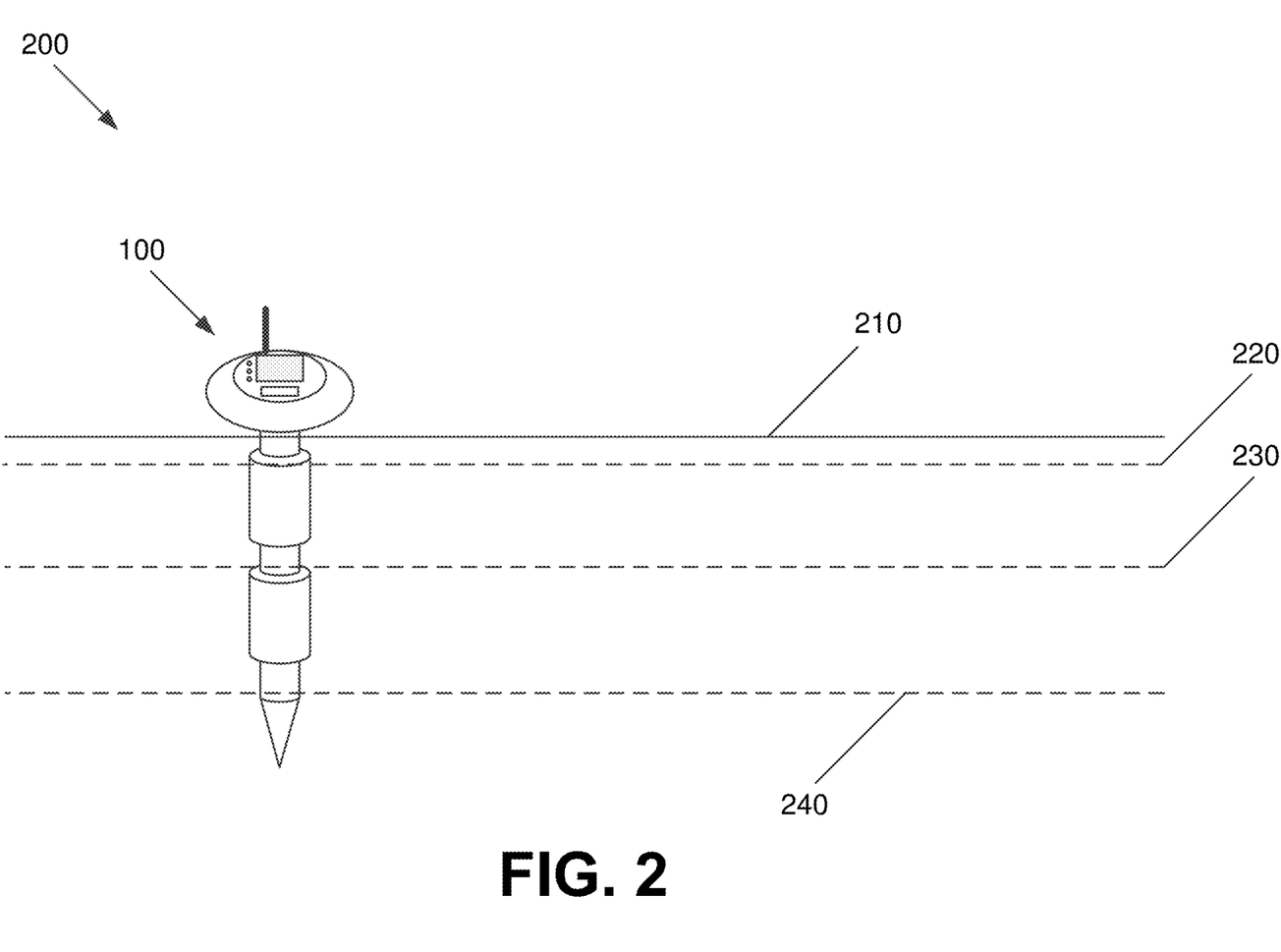
FIG. 2 illustrates the modular soil and water analysis device deployed in an environment, according to an embodiment of the present invention.

FIG. 2 illustrates modular soil and water analysis device 100 in a deployed environment 200, according to an embodiment of the present invention. Device 100 is deployed in ground or water 210. Sensor rod 110 is located at a depth between layer 220 and 230, whereas sensor rod 220 is located at a depth between layer 230 and 240. Sensor bus head 130 is above ground or water 210, and sensor bus terminus 150 is present below layer 240. The sensor(s) of first sensor rod 110 measure their respective parameters and communicate these parameters to sensor bus head 130. Sensor rod 110 sends the data from its analysis along with an indication the depth at which it is located. Similarly, sensor rod 120 communicates the sensor results, along with the depth at which its analysis is performed, to sensor bus head 130.

Figure 3:
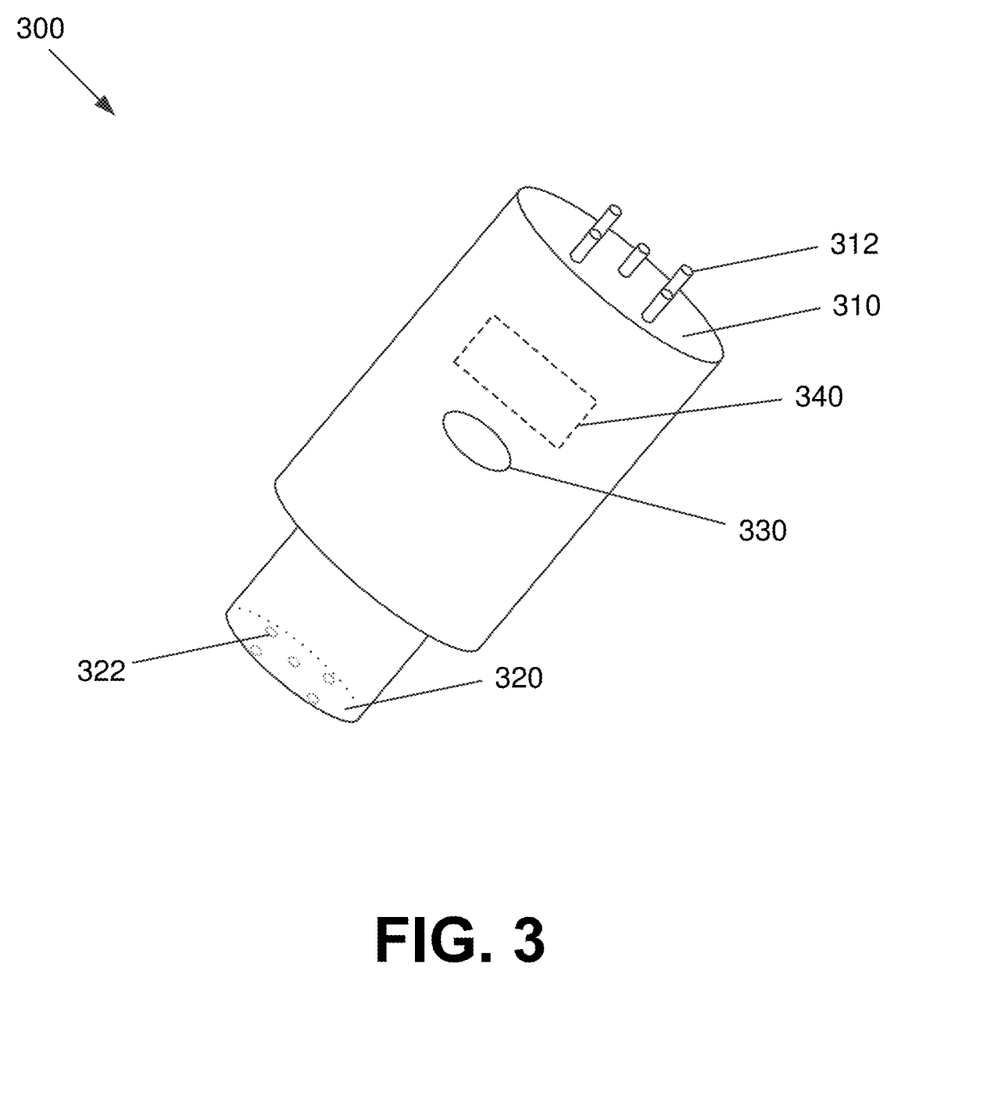
FIG. 3 is a perspective view illustrating a sensor rod, according to an embodiment of the present invention.

FIG. 3 is a perspective view illustrating a sensor rod 300, according to an embodiment of the present invention. Sensor rod 300 includes an upper section 310 including male connectors 312 and a lower section 320 including female connectors. Sensor rod 300 also includes a sensor 330 configured to measure a parameter (or multiple parameters). For instance, in some embodiments, sensor 330 may be an electrode used to measure analyte concentration. A microcontroller 340 is programmed to perform the various functions associated with sensor rod 300 and to communicate with a sensor bus head and a sensor bus terminus.

Figure 4:
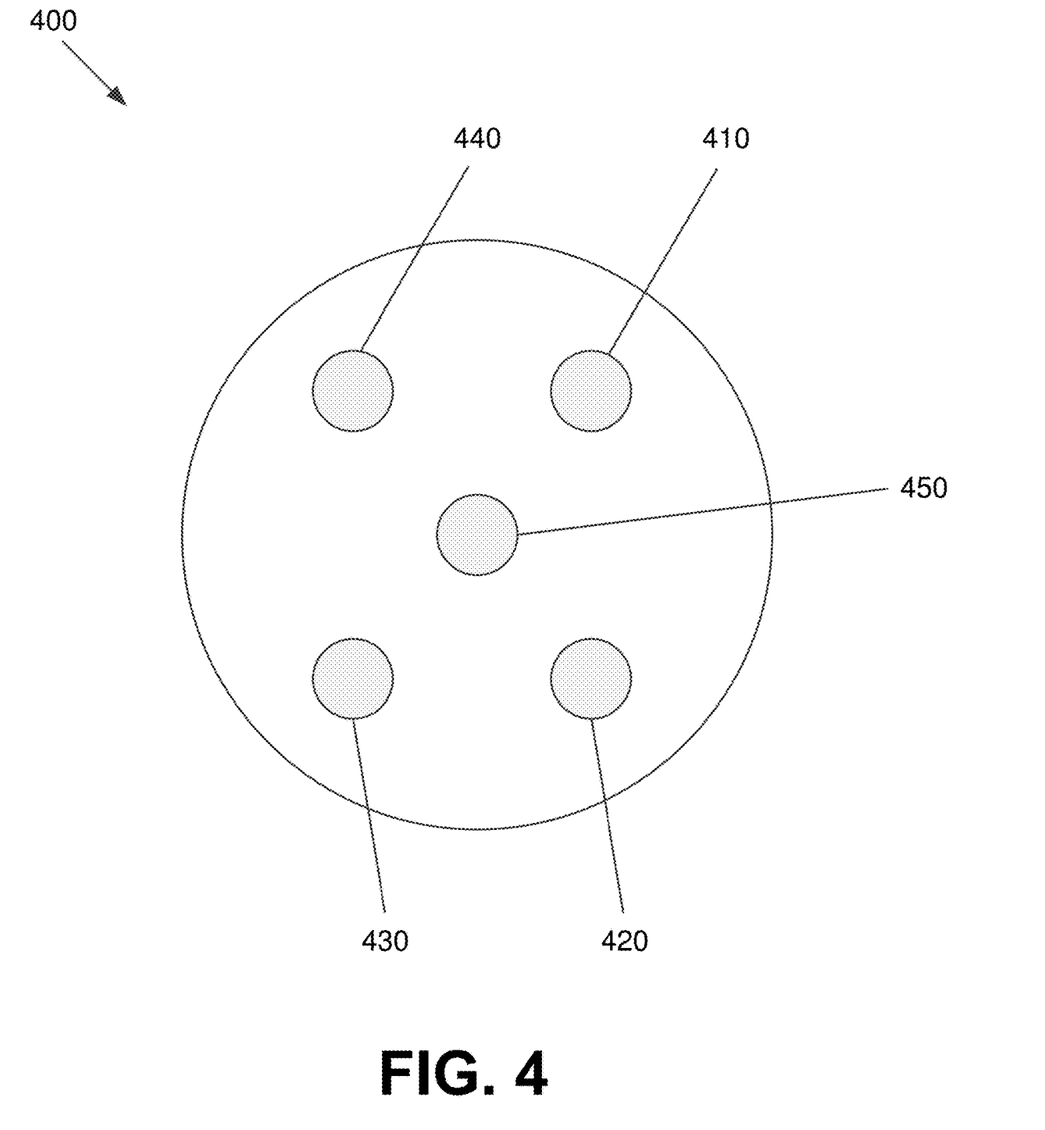
FIG. 4 is a top view illustrating sensor rod connectors, according to an embodiment of the present invention.

FIG. 4 is a top view illustrating connectors of a sensor rod 400, according to an embodiment of the present invention. Connector (e.g., pin) 410 is a power (Vcc) pin, where the sensor head will provide supply voltage to connector 410 when it is communicating with sensor rod 400, or other interconnected sensor rods. Connector 410 is shared by all the sensor rods present in the device in this embodiment. To save power, the sensor bus head may turn off the supply voltage when possible without interfering with sensor operations. Connector 420 is a ground (Gnd) pin, which is the reference ground for the entire system in this embodiment. Connector 420 may be shared by all sensor rods in the device. Connector 430 is a data pin that facilitates bidirectional communication between the sensor rods and the sensor bus head. Connector 440 is a clock (CLK) pin that is shared by all stacked sensor rods and is controlled by the sensor bus head. Connector 440 signals the rate at which information is clocked in and out of the sensor rods. Connector 450 is a sensor select SS pin (in/out) and is not shared by all stacked sensor rods in this embodiment. Rather, SS pins are daisy chained. Connector 450 in this embodiment is connected to the SS In pin of the stacked sensor (or sensor bus head) above it.

Figure 5:
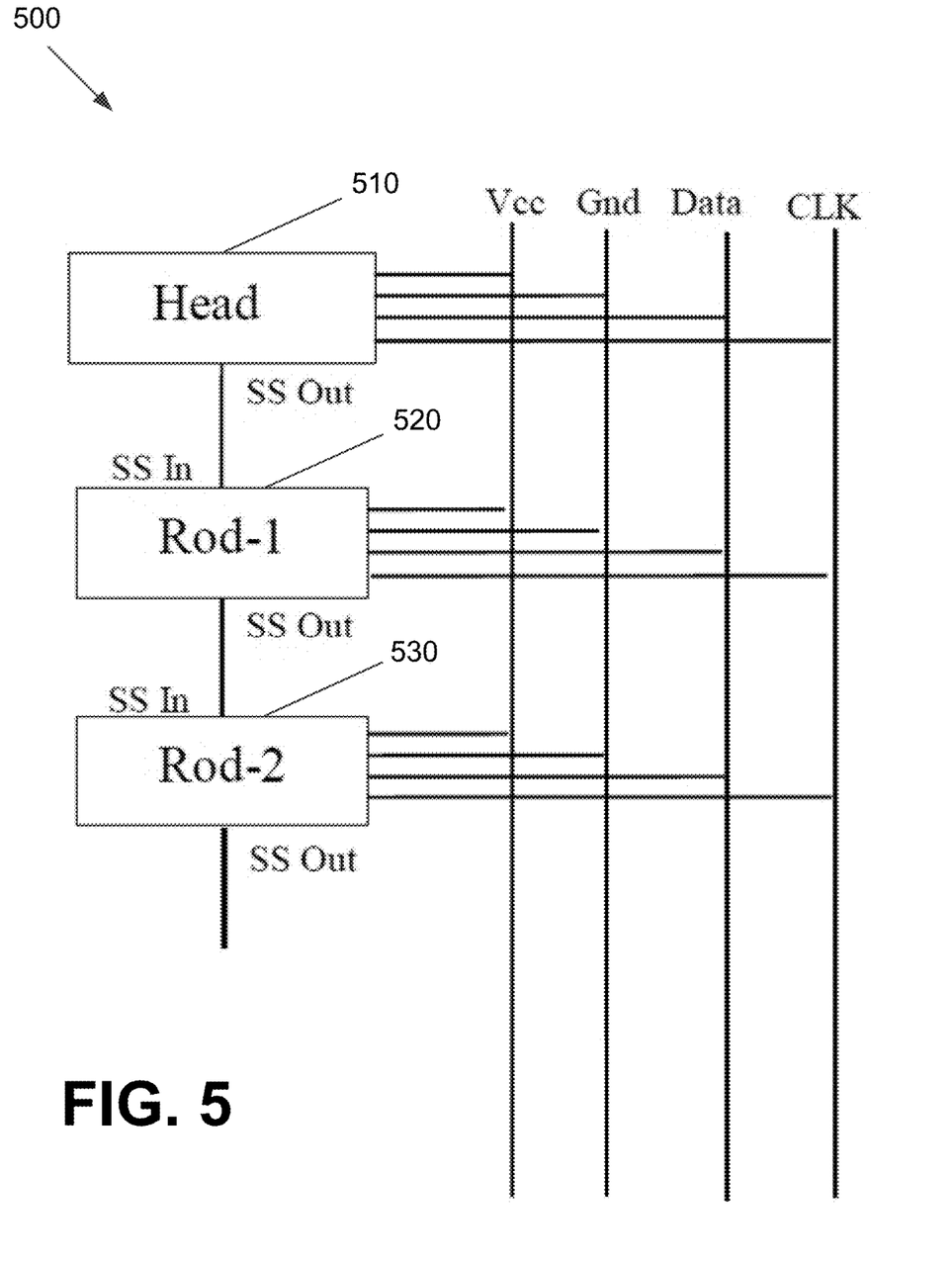
FIG. 5 is a wiring diagram illustrating bus architecture for stacked sensor rods, according to an embodiment of the present invention.

FIG. 5 is a wiring diagram 500 illustrating bus architecture for stacked sensor rods, according to an embodiment of the present invention. Sensor bus head 510 periodically communicates with sensor rods, such as sensor rods 520, 530, to query for sensor data or to instruct the system to perform certain instructions. In some embodiments, sensor rods 520, 530 may be stacked, and any desired number of sensor rods may be interconnected without deviating from the scope of the invention.

As shown in FIG. 5, all components (sensor bus head 510, sensor rod 520, and sensor rod 530) are connected to Vcc, Gnd, Data, and CLK lines. However, the SS connectors are "daisy chained" together. For instance, SS Out of sensor bus head 510 is connected to SS In of sensor rod 520, SS Out of sensor rod 520 is connected to SS In of sensor rod 530, etc. Through this configuration, individual sensor rods can be "awakened" to carry out their various functions.

Figure 6:
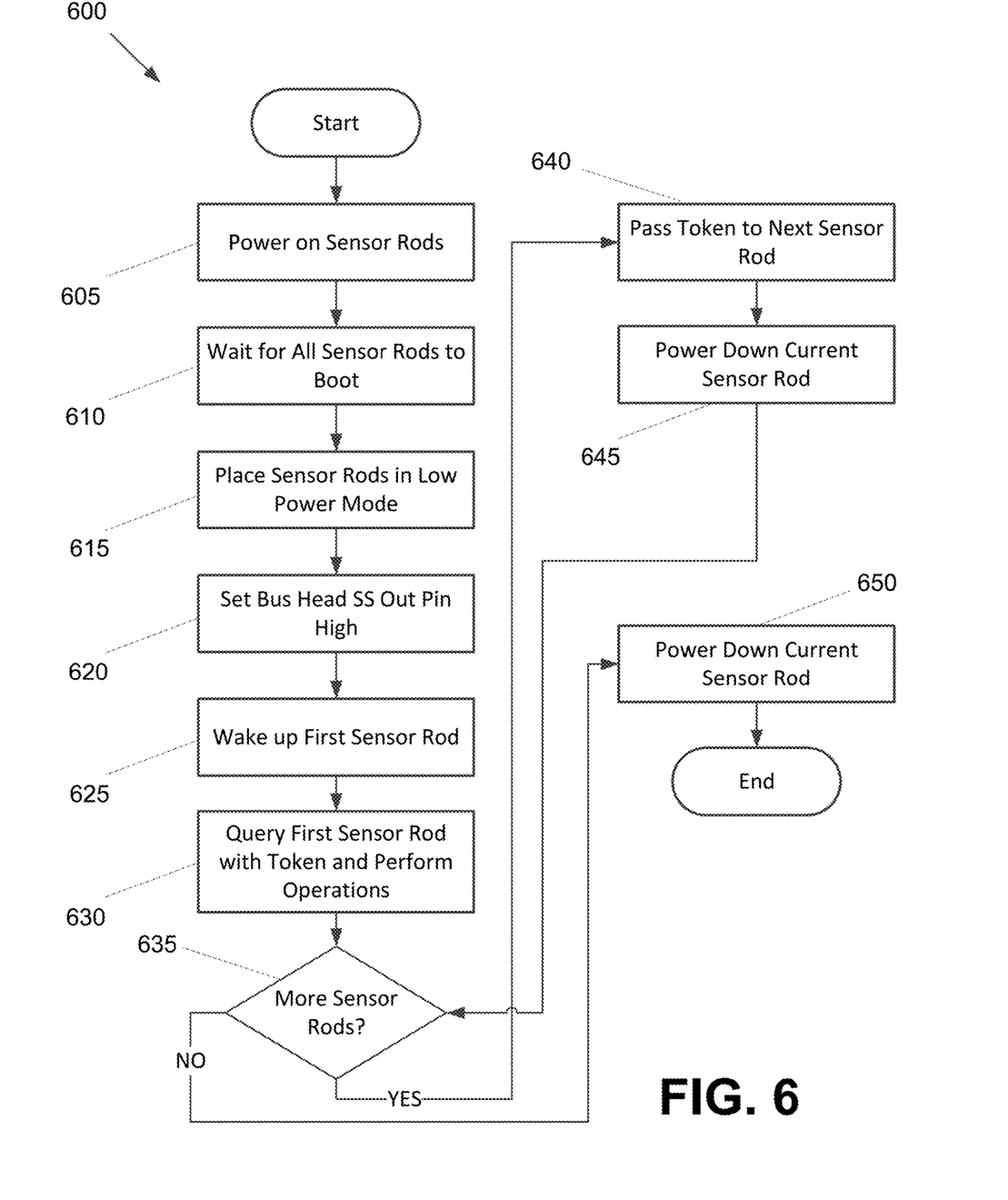
FIG. 6 is a flowchart illustrating a process for communication in a stacked sensor system, according to an embodiment of the present invention.

FIG. 6 is a flowchart 600 illustrating a process for communication in a stacked sensor system, according to an embodiment of the present invention. The process begins with powering on the sensor rods at 605. Initially, the sensor bus head may power on the sensor rods by providing a supply voltage at a Vcc pin. This turns ON all sensor rods that are connected to the sensor bus head. The sensor bus head then waits for all of the sensor rods to power up and go through their boot up sequence at 610. At the end of the boot up sequence, the sensor rods place themselves in a low power mode where their consumed current is the minimal leakage current at 615.

More specifically, during the boot-up sequence for each sensor rod, the sensor rods setup a low-to-high transition interrupt in the SS In pin, and, in addition, set their SS Out pins to a low state. Subsequently, each sensor rod goes into a low power mode, from which it awakens only by a low-to-high transition in voltage at the SSin pin in some embodiments. After waiting for the sensor rods to finish their bootup sequence, and when the sensor bus head is ready to communicate with the first sensor rod, the sensor bus head sets its SS Out pin to high at 620. The first sensor rod, which is directly attached to the sensor bus head, then sees the transition to high in its SS In pin and wakes up from its low power state at 625. At this point, the first sensor rod is fully "awake" and able to initiate a bidirectional communication with the sensor bus head as the first sensor rod has the communication token from the sensor bus head.

As used herein, a "token" is merely an abstraction. It is not a data format or a message. Rather, the token implies that whichever sensor rod is currently able to engage in a bidirectional communication with the sensor bus head is said to have the "token." When a sensor rod is in low power mode, it doesn't have the ability to engage in communication. The way some embodiments operate is that the sensor rod that is out of low power mode and is engaged in bidirectional communication with the sensor bus head will, at the end of its communication slot, be able to wake up the next sensor rod down in the stack and then put itself into low power sleep mode. This is called "passing the token."

Since the first sensor rod is the only rod that is currently out of the low power sleep mode, it is now able to engage in bidirectional communication with the sensor bus head. The sensor bus head will now be able to query the first sensor rod to get sensor data, pass calibration information, and finally, when the sensor bus head is done with the first sensor rod, it will instruct the first sensor rod to wake up the next sensor rod in the modular stack. The first sensor rod will then place itself in low power deep sleep mode (passing the token).

The sensor bus head then queries the first sensor rod with the token at 630, which may request communication of sensor data, pass sensor calibration information, and at the end, command the first sensor rod to pass the token to the next sensor rod in the stacked sensor arrangement, etc. Passing the token is the last command from sensor bus head to the first sensor rod in this embodiment.

If there are more sensor rods at 635 (i.e., there is more than one stacked sensor rod), the first sensor rod passes the token to the next sensor rod at 640 and powers down to the low power state at 645. More specifically, on receiving the pass token command, the first sensor rod will set its SS Out pin to high, pass the token, and then go into low power mode. The process then returns to step 635 and repeats as long as there are more sensor rods. More specifically, the next stacked sensor rod in the stacked chain is awakened from its low power state by the voltage level transition in its SS In pin.

However, if there are not more sensor rods (for instance, the sensor bus head observes that a communication attempt with the next sensor rod is resulting in no response), this indicates that the end of the sensor rod stack has been reached, and there is no further sensor rod connected in the stacked arrangement. The current sensor rod (i.e., the one currently with the token) then powers down to a low power state at 650. The process of waking up sensor rods and passing tokens may be repeated periodically to perform sensor operations, receive sensor data at the sensor bus head, and communicate the sensor data.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A modular sensor system comprising:
a sensor bus head including processing and control circuitry facilitating operation of the sensor bus head, and sensor bus connectors facilitating electrical communication between the modular sensor system;
a multi-part probe configured to couple to the sensor bus head and configured to electrically communicate with the sensor bus head in order to sense and communicate environmental parameters at one or more distances relative to the sensor bus head, the multi-part probe including:
a sensor bus terminus forming a terminal end of the modular probe and including sensor bus terminus connectors; and
a first sensor rod including first top end connectors interconnectable with the sensor bus connectors, and first bottom end connectors interconnectable with the sensor bus terminus connectors, wherein interconnection of the first sensor rod with the sensor bus terminus and the sensor bus head forms an interconnected bus network and a structural connection for the modular sensor system that facilitates sensing and communicating environmental parameters from the first sensor rod to the sensor bus head, wherein a second sensor rod is interconnectable between the sensor bus head and the sensor bus terminus to extend a length of the multi-part probe and to facilitate sensing and communication environmental parameters from both the first and second sensor rods to the sensor bus head.

2. The modular sensor system of claim 1, further comprising the second sensor rod including second top end connectors, and second bottom end connectors.

3. The modular sensor system of claim 2, wherein the first and second sensor rods are hot swappable to enable a multi-part probe of different lengths in order to sense environmental parameters at different distances from the sensor bus head.

4. The modular sensor system of claim 2, wherein the environmental parameters include one or more of soil, and water.

5. The modular sensor system of claim 2, wherein the environmental parameters include chemical composition of soil and/or water, pressure, temperature, and/or moisture, or any combination thereof.

6. The modular sensor system of claim 1, wherein the power and control interface comprises a solar panel, controls, and a display.

7. The modular sensor system of claim 1, wherein the sensor bus head comprises an antenna and circuitry that transmit analysis data to one or more other modular sensor systems, a central server via a cellular network, a local area network (LAN), a wide area network (WAN), a satellite communications network, or any combination thereof.

8. The modular sensor system of claim 1, wherein the at least one sensor rod is configured to communicate its depth to the sensor bus head.

9. The modular sensor system of claim 1, wherein the sensor bus connectors, the sensor bus terminus connectors, the first top end connectors, and the first bottom end connectors each comprises waterproof connectors comprising a power pin, a ground pin, a data pin, a clock pin, and a sensor select pin, wherein the power pin provides a supply voltage when communicating with the first sensor rod, the ground pin provides a reference ground for the sensor bus head, the sensor bus terminus, and the first sensor rod, the data pin facilitates bidirectional communication between the first sensor rod and the sensor bus head, the clock pin being controlled by the sensor bus head, and the sensor select pin is daisy chained and selects a current sensor rod that the sensor bus head is communicating with.

* * * * *